United States Patent [19]
Andersen et al.

[11] Patent Number: 6,004,983
[45] Date of Patent: *Dec. 21, 1999

[54] N-SUBSTITUTED AZAHETEROCYCLIC COMPOUNDS

[75] Inventors: Henrik Sune Andersen, København; Tine Krogh Jørgensen, Herlev; Rolf Hohlweg, Kvistgaard; Knud Erik Andersen, Smørum, all of Denmark; Zdenek Polivka, Praha 5; Frantisek Miksik, Praha 11, both of Czechoslovakia

[73] Assignee: Novo Nordisk A/S, Bagsvaerd, Germany

[ * ] Notice: This patent is subject to a terminal disclaimer.

[21] Appl. No.: 08/943,501

[22] Filed: Oct. 3, 1997

[30] Foreign Application Priority Data

Oct. 4, 1996 [DK] Denmark ................. 1088/96

[51] Int. Cl.⁶ .................. A61K 31/40; A61K 31/445; C07D 207/08; C07D 211/34
[52] U.S. Cl. .................. 514/325; 514/211; 514/217; 514/225.5; 514/320; 514/324; 514/422; 514/428; 540/550; 540/591; 544/46; 546/195; 546/196; 548/525; 548/528
[58] Field of Search .................. 514/211, 217, 514/225.5, 320, 324, 325, 428, 422; 540/550, 591; 544/46; 546/195, 196; 548/525, 528

[56] References Cited

U.S. PATENT DOCUMENTS

| | | | |
|---|---|---|---|
| 5,595,989 | 1/1997 | Andersen et al. | 514/217 |
| 5,688,788 | 11/1997 | Andersen et al. | 514/211 |
| 5,712,292 | 1/1998 | Andersen et al. | 514/325 |
| 5,716,949 | 2/1998 | Andersen et al. | 514/211 |
| 5,721,254 | 2/1998 | Andersen et al. | 514/324 |

FOREIGN PATENT DOCUMENTS

| | | |
|---|---|---|
| WO 95/18793 | 7/1995 | WIPO . |
| WO 96/31498 | 10/1996 | WIPO . |
| WO 96/31499 | 10/1996 | WIPO . |
| WO 97/22338 | 6/1997 | WIPO . |

OTHER PUBLICATIONS

Šindelár et al., Collect. Czech. Chem. Commun., vol. 59, pp. 667–674, (1994).

*Primary Examiner*—Mukund I. Shah
*Assistant Examiner*—Brenda Coleman
*Attorney, Agent, or Firm*—Steve T. Zelson; Valeta Gregg; Carol E. Rozek

[57] ABSTRACT

The present invention relates to novel N-substituted azaheterocyclic carboxcylic acids of the general formula

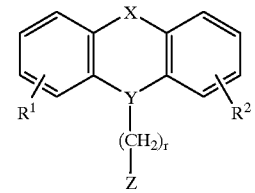

wherein X, Y, Z, $R^1$, $R^2$ and r are as defined in the detailed part of the description, or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation as well as their use for treatment of indications caused by or related to the secretion and circulation of insulin antagonising peptides.

18 Claims, No Drawings

N-SUBSTITUTED AZAHETEROCYCLIC COMPOUNDS

CROSS-REFERENCE TO RELATED APPLICATIONS

This application claims priority under 35 U.S.C. 119 of Danish application 1088/96 filed Oct. 4, 1996, the contents of which are fully incorporated herein by reference.

FIELD OF THE INVENTION

The present invention relates to novel N-substituted azaheterocyclic carboxylic acids in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for reducing blood glucose and/or inhibit the secretion, circulation or effect of insulin antagonizing peptides like CGRP or amylin, the present compounds being known to interfere with neuropeptide containing C-fibres. Hence the present compounds can be used in the treatment of insulin resistance in non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. No. 4,383,999 and No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

WO 9518793, published Jul. 13, 1995, WO 9631498 and WO 9631499, both published Oct. 10, 1996, discloses N-substituted azaheterocyclic carboxylic acids and esters thereof. However, none of the compounds of the present invention are specifically disclosed in the above mentioned WO publications.

SUMMARY OF THE INVENTION

The present invention relates to compounds of the general formula I, wherein X, Y, Z, $R^1$, $R^2$ and r are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, inflammation, migraine, neuropathy, itching and rheumatoid arthritis, as well as indications caused by or related to the secretion and circulation of insulin antagonising peptides, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM) and ageing-associated obesity. The method of treating may be described as the treatment of one of the above indications in a subject in need thereof, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic carboxylic acids of formula I

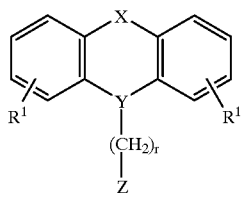

(I)

wherein

R[1] and R[2] independently are hydrogen, halogen or $C_{1-6}$-alkyl; and

Y is >N—CH$_2$— or >C=CH— wherein only the underscored atom participates in the ring system; and X is —S—, —CH$_2$CH$_2$—, —O—CH$_2$—, —CH$_2$—O—, —S—CH$_2$—, —CH$_2$—S—; and r is 1 or 2 ; and Z is selected from

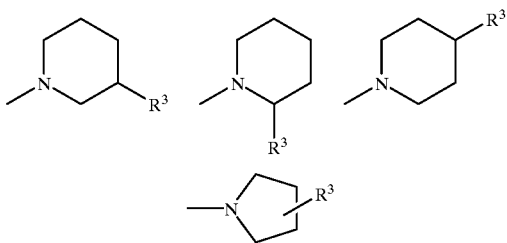

wherein R[3] is —(CH$_2$)$_p$COOH wherein p is 0 or 1; or a pharmaceutically acceptable salt thereof.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "halogen" means fluorine, chlorine, bromine or iodine.

Illustrative examples of compounds encompassed by the present invention include:

1-(2-(6,11-Dihydrodibenzo[b,e]thiepin-11-ylidene)-1-ethyl)-3-piperidinecarboxylic acid;

1-(2-(6,11-Dihydrodibenzo[b,e]thiepin-11-ylidene)-1-ethyl)-4-piperidinecarboxylic acid;

1-(2-(2-Chloro-6,11-dihydrodibenzo[b,e]thiepin-11-ylidene)-1-ethyl)-3-piperidinecarboxylic acid;

1-(2-(2-Chloro-6,11-dihydrodibenzo[b,e]thiepin-11-ylidene)-1-ethyl)-4-piperidinecarboxylic acid;

(R)-1-(2-(6,11-Dihydrodibenzo[b,e]thiepin-11-ylidene)-1-ethyl)-3-piperidinecarboxylic acid;

1-(3-(2-Bromo-10,11-dihydro-5H-dibenzo[a,d]cyclohepten-5-ylidene)-1-propyl)-3-pyrrolidineacetic acid;

1-(3-(3-Methyl-10,11-dihydro-5H-dibenzo[a,d]cyclohepten-5-ylidene)-1-propyl)-3-pyrrolidineacetic acid;

1-(3-(6,11-Dihydro-dibenz[b,e]thiepin-11-ylidene)-1-propyl)-4-piperidinecarboxylic acid;

1-(3-(2-Fluoro-10,11-dihydro-5H-dibenzo[a,d]cyclohepten-5-ylidene)-1-propyl)-4-piperidinecarboxylic acid;

1-(3-(10,11-Dihydro-5H-dibenzo[b,f]azepin-5-yl)-1-propyl)-2-piperidineacetic acid;

1-(3-(Phenothiazin-10-yl)-1-propyl)-4-piperidinecarboxylic acid;

(R)-1-(2-(10,11-dihydro-5H-dibenzo[a,d]cyclohepten-5-ylidene)-1-ethyl)-2-piperidinecarboxylic acid;

1-(2-(10,11-Dihydro-5H-dibenzo[a,d]cyclohepten-5-ylidene)-1-ethyl)-4-piperidinecarboxylic acid;

1-(2-(6,11-Dihydrodibenzo[b,e]oxepin-11-ylidene)-1-ethyl)-4-piperidinecarboxylic acid;

or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i. e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I improve the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

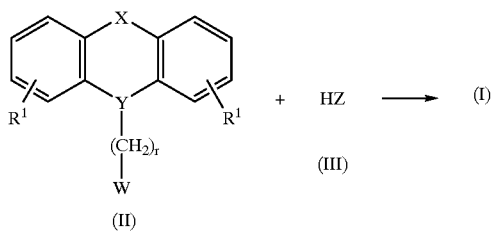

A compound of formula II wherein $R^1$, $R^2$, X, Y and r are as defined above and W is a suitable leaving group such as halogen, p-toluene sulphonate or mesylate may be reacted with an aza compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

I. Histamine induced paw oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree(Celsius) heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

TABLE 1

Inhibition of histamine induced oedema at 1 mg/kg

| Example No. | % oedema inhibition |
|---|---|
| 2 | 51 |
| 12 | 49 |

II. Reduced release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunk blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

PHARMACEUTICAL COMPOSITIONS

The present invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

The route of administration may be any route which effectively transports the active compound to the appropriate or desired site of action, such as oral, nasal, pulmonary or parenteral e.g. rectal, depot, transdermal, subcutaneous, intranasal, intramuscular, topical, intravenous, intraurethral, ophthalmic solution or an ointment, the oral route being preferred.

If a solid carrier for oral administration is used, the preparation can be tabletted, placed in a hard gelatine capsule in powder or pellet form or it can be in the form of a troche or lozenge.

The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

Suitable dosage ranges varies as indicated above depending as usual upon the exact mode of administration, form in which administered, the indication towards which the administration is directed, the subject involved and the body weight of the subject involved, and the preference and experience of the physician or veterinarian in charge.

Generally, the compounds of this invention are dispensed in unit dosage form comprising 50–200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(2-(6,11-Dihydrodibenzo[b,e]thiepin-11-ylidene)-1-ethyl)-3-piperidinecarboxylic acid hydrochloride

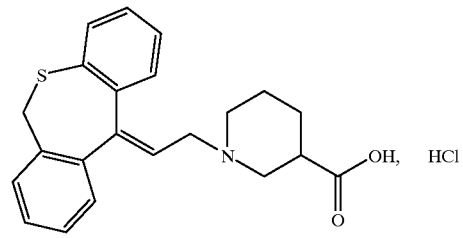

To a solution of 11-(2-bromoethylidene)-6,11-dihydrodibenzo[b,e]thiepine (3.33 g, 0.0105 mol, prepared similarly as described in Coll.Czech.Chem.Comm. 52, 1566, 1987) in dimethylsulfoxide (60 ml), potassium carbonate (2.0 g, 0.02 mol), 3-piperidinecarboxylic acid ethyl ester (1.65 g, 0.0105 mol) and sodium iodide (50 mg) were added and the mixture was stirred at 50° C. for 4 h. The reaction mixture was diluted with chloroform (100 ml), the solid was filtered off and the filtrate was washed with water (3×80 ml). The chloroform solution was dried ($MgSO_4$) and the solvent removed in vacuo. The oily residue (5.6 g) was dissolved in acetone and treated with an ethanolic solution of oxalic acid. The crude hydrogen oxalate (5.8 g) was filtered off and washed with a hot mixture of ethanol and acetone. This afforded 3.81 g (75%) of 1-(2-(6,11-dihydrodibenzo[b,e]thiepin-11-ylidene)-1-ethyl)-3-piperidinecarboxylic acid ethyl ester hydrogen oxalate.

The above ester (2.95 g base liberated from the hydrogen oxalate, 0.0075 mol) was dissolved in ethanol (50 ml) and 15% sodium hydroxide (11 ml) was added. The reaction mixture was stirred at room temperature for 10 h, then poured into dichloromethane (500 ml) and acidified with concentrated hydrochloric acid. The dichloromethane layer was separated, dried ($MgSO_4$) and evaporated in vacuo. The residue was crystallised from a mixture of 95% ethanol and ether to give 2.7 g (90%) of the title compound.

M.p. 227–240° C. Calculated for $C_{22}H_{23}NO_2S$, HCl: C, 65.74%; H, 6.02%; Cl, 8.82%; N, 3.49%; S, 7.98%; Found: C, 65.53%; H, 6.18%; Cl, 8.76%; N, 3.44%; S, 7.82%.

Example 2

1-(2-(6,11-Dihydrodibenzo[b,e]thiepin-11-ylidene)-1-ethyl)-4-piperidinecarboxylic acid hydrochloride

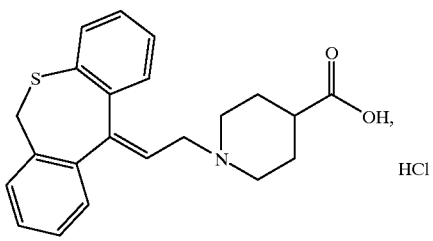

To a solution of 11-(2-bromoethylidene)-6,11-dihydrodibenzo[b,e]thiepine (4.76 g, 0.015 mol, prepared similarly as described in Coll. Czech. Chem. Comm. 52, 1566, 1987) in dimethylsulfoxide (90 ml), potassium carbonate (3.1 g, 0.0225 mol), 4-piperidinecarboxylic acid ethyl ester (2.36 g, 0.015 mol) and sodium iodide (50 mg) were added and the mixture was stirred at 100° C. for 4 h. The reaction mixture was diluted with benzene (100 ml), the solid was filtered off and the filtrate was washed with water (4×60 ml). The benzene solution was dried (MgSO$_4$) and the solvent removed in vacuo. The oily residue (6.34 g) was dissolved in acetone and treated with an ethanolic solution of oxalic acid. The resulting precipitate was filtered off and washed with a hot mixture of ethanol and acetone, affording 5.2 g (72%) of 1-(2-(6,11-dihydrodibenzo[b,e]thiepin-11-ylidene)-1-ethyl)-4-piperidinecarboxylic acid ethyl ester hydrogen oxalate.

The above ester (3.95 g base liberated from the hydrogen oxalate, 0.01 mol) was dissolved in ethanol (30 ml) and 4 N sodium hydroxide (8 ml) was added. The reaction mixture was stirred at room temperature for 15 h, then poured into dichloromethane (250 ml) and acidified with concentrated hydrochloric acid. The dichloromethane layer was separated, dried (MgSO$_4$) and evaporated in vacuo. The residue was re-evaporated twice with acetone (15 ml) and the crude product was dissolved in acetone (30 ml). The product was filtered off and washed with diethyl ether. After drying, this afforded 3.71 (92%) of the title compound.

M.p. 227–240° C. Calculated for $C_{22}H_{23}NO_2S$, HCl C, 65.74%; H, 6.02%; Cl, 8.82%; N, 3.49%; S, 7.98%. Found: C, 65.39%; H, 6.15%; Cl, 8.55%; N, 3.34%; S, 7.63%

Example 3

1-(2-(2-Chloro-6,11-dihydrodibenzo[b,e]thiepin-11-ylidene)-1-ethyl)-3-piperidinecarboxylic acid hydrochloride

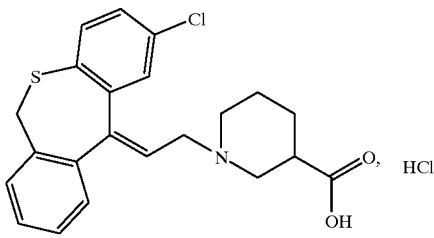

Magnesium (4.94 g, 0.203 mol) under tetrahydrofuran (15 ml) was activated with a grain of iodine and 1,2-dibromoethane (0.4 ml). After the reaction was finished, 10% of a solution of vinylbromide (21.4 g, 0.2 mol) in tetrahydrofuran (70 ml) was added (dry ice-ethanol condenser, nitrogen atmosphere). The reaction started immediately, and the remaining part of the vinylbromide solution was added dropwise under stirring at such a rate (over 45 minutes) as to maintain the temperature at 58–62° C. The mixture was heated at reflux temperature for 30 minutes and then cooled to 30° C. Over 1 h, a solution of 2-chloro-6,11-dihydrodibenzo[b,e]thiepine (28.9 g, 0.1 mol, prepared as described in Ès. farmacie 11, 451, 1962) in tetrahydrofuran (70 ml) was added dropwise under stirring (30–35° C.). The mixture was allowed to stand overnight at room temperature and then quenched under cooling (ice and sodium chloride) with a solution of ammonium chloride (21 g) in water (100 ml). Toluene (100 ml) was added, the mixture was filtered and the aqueous layer was extracted with toluene (3×100 ml). The toluene solutions were combined, dried (MgSO$_4$) and evaporated. The residue was crystallised from a mixture of benzene (50 ml) and hexane (100 ml) to give 27.4 g (95%) of 2-chloro-11-vinyl-6,11-dihydrodibenzo[b,e]thiepin-11-ol.

A suspension of the above alcohol (25.3 g, 0.0876 mol) in acetic acid (350 ml) was stirred and treated at 15° C. with a 15% solution of hydrobromic acid in acetic acid (48 ml) over 30 minutes. The mixture was stirred at 15° C. for 1 h, then filtered, and the solid was washed with water (3×60 ml), acetic acid (100 ml) and dried. Yield 25.6 g (83%) of 11-(2-bromoethylidene)-2-chloro-6,11-dihydrodibenzo[b,e]thiepine.

To a solution of the above bromide (1.76 g, 0.005 mol) in dimethylsulfoxide (30 ml), potassium carbonate (0.82 g, 0.006 mol), 3-piperidinecarboxylic acid ethyl ester (0.86 g, 0.0055 mol) and sodium iodide (20 mg) were added, and the mixture was stirred at 50° C. for 4 h. The reaction mixture was diluted with chloroform (100 ml), the solid was filtered off and the filtrate was washed with water (3×40 ml). The chloroform solution was dried (MgSO$_4$) and the solvent evaporated in vacuo. The oily residue (2.53 g) was dissolved in acetone and treated with an ethanolic solution of oxalic acid. The precipitated crude hydrogen oxalate salt (2.55 g) was recrystallised from aqueous ethanol, to give 1.84 g (71%) of 1-(2-(2-chloro-6,11-dihydrodibenzo[b,e]thiepin-11-ylidene)-1-ethyl)-3-piperidinecarboxylic acid ethyl ester hydrogen oxalate.

The above ester (1.0 g base liberated from the hydrogen oxalate, 0.0025 mol) was dissolved in ethanol (25 ml) and 20% sodium hydroxide (10 ml) was added. The reaction mixture was stirred at room temperature for 10 h, then poured into dichloromethane (350 ml) and acidified with concentrated hydrochloric acid. The dichloromethane layer was separated, dried (MgSO$_4$) and evaporated in vacuo. The residue was crystallised from a mixture of 95% ethanol and acetone, affording 0.47 g (43%) of the title compound.

M.p. 235–250° C. (decomp.). Calculated for $C_{22}H_{22}ClNO_2S$, HCl: C, 60.55%; H, 5.31%; Cl, 16.25%; N, 3.21%; S, 7.33%. Found: C, 60.74%; H, 5.33%; Cl, 16.47%; N, 2.93%; S, 7.28%

Example 4

1-(2-(2-Chloro-6,11-dihydrodibenzo[b,e]thiepin-11-ylidene)-1-ethyl)-4-piperidinecarboxylic acid hydrochloride

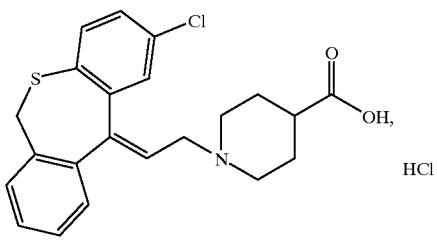

To a solution of 11-(2-bromoethylidene)-2-chloro-6,11-dihydrodibenzo[b,e]thiepine (1.76 g, 0.005 mol, prepared as described in Example 3) in N,N-dimethylformamide (20 ml), potassium carbonate (2.33, 0.006 mol) and 4-piperidinecarboxylic acid ethyl ester (0.86 g, 0.0055 mol) were added and the mixture was stirred at 50° C. for 3 h. The reaction mixture was diluted with dichloromethane (80 ml), the solid was filtered off and the filtrate was washed with water (4×30 ml). The dichloromethane solution was dried (MgSO$_4$) and the solvent removed in vacuo. The oily residue (2.34 g) was dissolved in acetone and treated with an ethanolic solution of oxalic acid. The precipitated crude hydrogen oxalate salt (5.8 g) was recrystalised from aqueous ethanol, to give 1.12 g (87%) of 1-(2-(2-chloro-6,11-dihydrodibenzo[b,e]thiepin-11-ylidene)-1-ethyl)-4-piperidinecarboxylic acid ethyl ester hydrogen oxalate.

The above ester (0.70 g base liberated from the hydrogen oxalate, 0.0017 mol) was dissolved in ethanol (25 ml) and 40% sodium hydroxide (6 ml) was added. The reaction mixture was stirred and heated at reflux temperature for 1 h, cooled and then poured into dichloromethane (150 ml). The solution was acidified with concentrated hydrochloric acid, the dichloromethane layer was separated, dried (MgSO$_4$) and evaporated in vacuo. This afforded 0.71 g (96%) of crude hydrochloride of the title compound, which was recrystallised from a mixture of acetone and diethyl ether.

M.p. 230–250° C. (decomp.). Calculated for C$_{22}$H$_{22}$ClNO$_2$S, HCl C, 60.55%; H, 5.31%; Cl, 16.25%; N, 3.21%; S, 7.33%. Found: C, 60.29%; H, 5.32%; Cl, 16.09%; N, 2.90%; S, 7.44%.

Example 5
(R)-1-(2-(6,11-Dihydrodibenzo[b,e]thiepin-11-ylidene)-1-ethyl)-3-piperidinecarboxylic acid hydrochloride

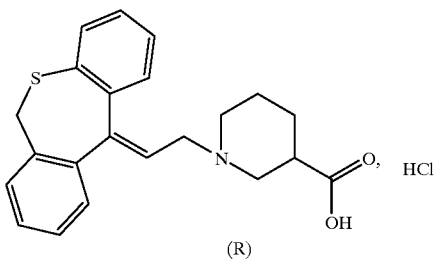

To a solution of 11-(2-bromoethylidene)-6,11-dihydrodibenzo[b,e]thiepine (4.43 g, 0.014 mol, Coll.Czech.Chem.Comm. 52, 1566 (1987)) in N,N-dimethylformamide (75 ml), potassium carbonate (19.3 g, 0.14 mol) and (R)-3-piperidinecarboxylic acid ethyl ester tartrate (6.43 g, 0.0209 mol) were added and the mixture was stirred at 70° C. for 6 h. The reaction mixture was diluted with benzene (300 ml), the solid was filtered off and the filtrate was washed with water (5×80 ml). The benzene solution was dried (MgSO$_4$) and the solvent removed in vacuo. The oily residue (6.83 g) was dissolved in acetone and treated with a solution of oxalic acid in ethanol. The solid was isolated and the crude hydrogen oxalate (5.8 g) was recrystallised from a mixture of 96% ethanol and ether to yield 5.81 g (86%) of (R)-1-(2-(6,11-dihydrodibenzo[b,e]thiepin-11-ylidene)-1-ethyl)-3-piperidinecarboxylic acid ethyl ester hydrogen oxalate.

M.p. 170–173° C.

The above ester (4.70 g base liberated from the hydrogen oxalate, 0.012 mmol) was dissolved in ethanol (30 ml) and 4 N sodium hydroxide (9 ml) was added. The reaction mixture was stirred at room temperature for 6 h, poured into dichloromethane (400 ml) and acidified with concentrated hydrochloric acid. The dichloromethane layer was separated, dried (MgSO$_4$) and evaporated in vacuo. The oily residue was stripped twice with acetone and then triturated with hot acetone which afforded 3.86 g (83%) of the title compound.

M.p. 220–227° C. Calculated for C$_{22}$H$_{23}$NO$_2$S, HCl C, 65.74%; H, 6.02%; Cl, 8.82%; N, 3.49%; S, 7.98%. Found: C, 65.82%; H, 6.09%; Cl, 8.79%; N, 3.44%; S, 8.08%.

Example 6
1-(3-(2-Bromo-10,11-dihydro-5H-dibenzo[a,d]cyclohepten-5-ylidene)-1-propyl)-3-pyrrolidineacetic acid hydrochloride

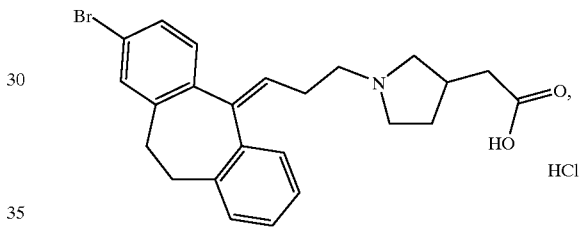

HPLC retention time=20.07 and 20.26 minutes (mixture of E/Z-isomers)(5 μm C18 4×250 mm column, eluting with a 20–80% gradient of 0.1% trifluoroacetic acid/acetonitrile and 0.1% trifluoroacetic acid/water over 25 minutes at 35° C.).

Calculated for C$_{24}$H$_{26}$BrNO$_2$, HCl, 0.5H$_2$O: C, 59.33%; H, 5.81%; N, 2.88%; Found: C, 59.34%; H, 5.97%; N, 2.56%.

Example 7
1-(3-(3-Methyl-10,11-dihydro-5H-dibenzo[a,d]cyclohepten-5-ylidene)-1-propyl)-3-pyrrolidineacetic acid, hydrochloride

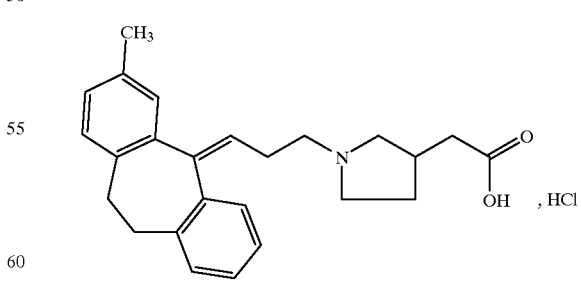

HPLC retention time=18.91 and 19.06 minutes (mixture of E/Z-isomers)(5 μm C18 4×250 mm column, eluting with a 20–80% gradient of 0.1% trifluoroacetic acid/acetonitrile and 0.1 % trifluoroacetic acid/water over 25 minutes at 35° C.

Calculated for $C_{25}H_{29}NO_2$, HCl, 0.75$H_2O$: C, 70.57%; H, 7.46%; N, 3.29%; Found: C, 70.45%; H, 7.36%; N, 3.04%.

Example 8

1-(3-(6,11-Dihydro-dibenz[b,e]thiepin-11-ylidene)-1-propyl)-4-piperidinecarboxylic acid hydrochloride

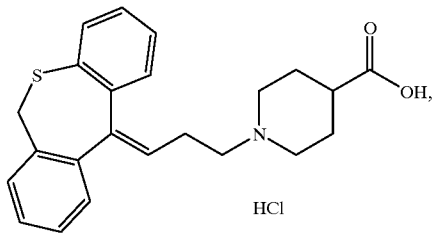

A solution of cyclopropylmagnesium bromide in dry tetrahydrofuran (prepared from cyclopropyl bromide (3.7 g, 0.031 mol), magnesium turnings (0.8 g, 0.033 mol) and dry tetrahydrofuran (50 ml) under an atmosphere of nitrogen) was added dropwise to a solution of (6,11-dihydrodibenzo[b,e]thiepin-11-one (3.5 g, 0.016 mol, prepared as described in Chem. Pharm. Bull. 39, 1991, 2564) in dry tetrahydrofuran (50 ml). When addition was complete, the mixture was heated at 50° C. for 2 h. The reaction mixture was cooled on an ice-bath and saturated ammonium chloride (50 ml) and water (50 ml) were carefully added. The mixture was extracted with diethyl ether (2×100 ml), dried (MgSO$_4$), filtered and the solvent was evaporated in vacuo to give 4.4 g of crude 11-cyclopropyl-6,11-dihydro-11H-dibenzo[b,e]thiepin-11-ol as an oil.

The above crude alcohol (4.0 g) was dissolved in dichloromethane (50 ml) and a solution of trimethylsilyl bromide (2.1 ml, 0.016 mol) was added dropwise at room temperature. When addition was complete the mixture was stirred at room temperature for 1.5 h and water (50 ml) was added. The phases were separated and the organic phase was washed with water (50 ml), dried (MgSO$_4$) and the solvent was evaporated in vacuo to give 4.1 g (83%) of crude 1-bromo-3-(6,11-dihydro-dibenzo[b,e]thiepin-11-ylidene) propane as a solid.

A mixture of the above crude bromide (1.0 g, 3.02 mmol), 4-piperidinecarboxylic acid ethyl ester (1.0 g, 6.04 mmol), dry potassium carbonate (2.5 g, 18.11 mmol), potassium iodide (1.0 g, 6.02 mmol) and methyl ethyl ketone (100 ml) was heated at reflux temperature for 18 h. The cooled reaction mixture was quenched with water (100 ml) and extracted with diethyl ether (100 ml). The combined organic extracts were extracted with 5 N hydrochloric acid (2×100 ml) and the aqueous phase was washed with diethyl ether (50 ml). The aqueous phase was basified with 50% sodium hydroxide and extracted with diethyl ether (2×100 ml). The combined organic extracts were washed with saturated aqueous ammonium chloride (100 ml), dried (MgSO$_4$), filtered and the solvent was evaporated in vacuo. This afforded 0.50 g (41%) of 1-(3-(6,11-dihydrodibenzo[b,e]thiepin-11-ylidene)-1-propyl)-4-piperidinecarboxylic acid ethyl ester as an oil.

TLC: R$_f$=0.28 (SiO$_2$: ethyl acetate/heptane=1:1)

The above ethyl ester (0.5 g, 1.23 mmol) was dissolved in ethanol (10 ml) and a solution of sodium hydroxide (60 mg, 1.47 mmol) in water (5 ml) was added. The reaction mixture was stirred for 18 h at room temperature and the solvent was removed in vacuo. Water (75 ml) was added, and the mixture was washed with diethyl ether (2×50 ml). The aqueous phase was acidified (pH=1) with concentrated hydrochloric acid and extracted with dichloromethane (3×50 ml). The combined organic extracts were washed with water (50 ml), dried (MgSO$_4$), filtered and the solvent was evaporated in vacuo. The residue was suspended in a mixture of acetone (5 ml) and diethyl ether (10 ml) and stirred for 18 h at room temperature. The precipitate was filtered off and washed with diethyl ether to give 0.25 g of a powder. This was suspended in dichloromethane (10 ml), filtered off, washed with a small portion of dichloromethane and dried. This afforded 55 mg (11%) of the title compound as an amorphous solid.

$^1$H NMR (400 MHz, DMSO-d$_6$) δ1.79 (m, 2H); 2.00 (m, 3H); 2.21 (m, 1H); 2.44 (m, 1H); 2.84 (m, 2H); 3.14 (m, 2H); 3.36 (m, 2H); 3.71 (d, 1H, J=13.8 Hz); 4.76 (d, 1H, J=13.8 Hz); 5.89 (t, 1H); 6.98 (dd, 1H); 7.11 (m, 3H); 7.32 (m, 3H); 7.45 (d, 1H); 10.1 (bs, 1H); 12.5 (bs, 1H).

MS (EI) 379 (M$^+$, 20%)

Example 9

1-(3-(2-Fluoro-10,11-dihydro-5H-dibenzo[a,d]cyclohepten-5-ylidene)-1-propyl)-4-piperidinecarboxylic acid, hydrochloride

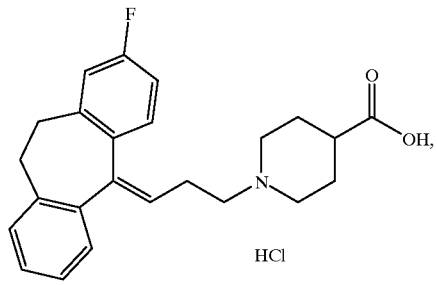

A solution of cyclopropylmagnesium bromide in dry tetrahydrofuran (prepared from cyclopropyl bromide (10.7 g, 0.088 mol), magnesium turnings (2.14 g, 0.088 mol) and dry tetrahydrofuran (100 ml) under an atmosphere of nitrogen) was added dropwise to a solution of 2-fluoro-10,11-dihydro-5H-dibenzo[a,d]cyclohepten-5-one (10.0 g, 0.044 mol) in dry tetrahydrofuran (100 ml). When addition was complete the mixture was heated at 50° C. for 3 h. The reaction mixture was cooled on an ice-bath and saturated ammonium chloride (50 ml) was added. The mixture was extracted with diethyl ether (2×100 ml) and the combined organic extracts were washed with saturated sodium chloride (50 ml), dried (MgSO$_4$), filtered and the solvent was evaporated in vacuo to give 11.2 g of crude 2-fluoro-5-cyclopropyl-10,11-dihydro-5H-dibenzo[a,d]cycloheptan-5-ol as an oil.

The above crude alcohol (10.0 g) was dissolved in dichloromethane (150 ml) and a solution of trimethylsilyl bromide (5.3 ml, 0.041 mol) was added dropwise at room temperature. When addition was complete, the mixture was stirred at room temperature for 1 h and water (50 ml) was added. The phases were separated and the organic phase was washed with water (50 ml), dried (MgSO$_4$) and the solvent was evaporated in vacuo to give 11.2 g (91%) of crude 1-bromo-3-(10,11-dihydro-5H-dibenzo[a,d]cycloheptan-5-ylidene)propane as a solid.

A mixture of the above crude bromide (3.0 g, 9.06 mmol), 4-piperidinecarboxylic acid ethyl ester (1.4 g, 18.12 mmol), dry potassium carbonate (7.5 g, 54.3 mmol), potassium iodide (1.5 g, 9.06 mmol) and methyl ethyl ketone (150 ml) was heated at reflux temperature for 18 h. The cooled reaction mixture was quenched with water (100 ml) and extracted with diethyl ether (2×100 ml). The combined organic extracts were washed with water (2×100 ml) and saturated sodium chloride (100 ml), dried (MgSO$_4$), filtered and the solvent was evaporated in vacuo. The residue (3.6 g) was purified by column chromatography on silica gel (1000 ml) using a mixture of ethyl acetate and heptane (1:1) as eluent. This afforded 1.6 g (43%) of 1-(3-(2-fluoro-10,11-dihydro-5H-dibenzo[a,d]cyclohepten-5-ylidene)-1-propyl)-4-piperidinecarboxylic acid ester as an oil.

The above ethyl ester (1.5 g, 3.69 mmol) was dissolved in 96% ethanol (30 ml) and a solution of sodium hydroxide (220 mg, 5.52 mmol) in water (15 ml) was added. The reaction mixture was stirred for 18 h at room temperature and the solvent was removed in vacuo. Water (100 ml) was added and the mixture was washed with diethyl ether (50 ml). The aqueous phase was acidified (pH=1) with concentrated hydrochloric acid and extracted with dichloromethane (3×75 ml). The combined organic extracts were dried (MgSO$_4$), filtered and the solvent evaporated in vacuo. The residue was suspended in acetone (25 ml) and stirred for 1 h at room temperature. The precipitate was filtered off, washed with diethyl ether and dried, to give 0.7 g of the title compound as an amorphous solid.

Calculated for $C_{24}H_{26}FNO_2$, HCl, 0.25H$_2$O: C, 68.56%; H, 6.59%; N, 3.33%; Found: C, 68.54%; H, 6.71%; N, 3.12%.

Example 10
1-(3-(10,11-Dihydro-5H-dibenzo[b,f]azepin-5-yl)-1-propyl)-2-piperidineacetic acid, hydrochloride

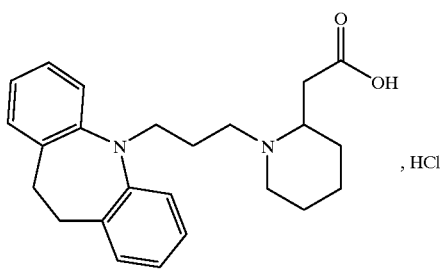

HPLC retention time=17.27 minutes (5 μm C18 4×250 mm column, eluting with a 20–80% gradient of 0.1% trifluoroacetic acid/acetonitrile and 0.1% trifluoroacetic acid/water over 25 minutes at 35° C.

Calculated for $C_{24}H_{30}N_2O_2$, HCl, 0.5H$_2$O: C, 67.99%; H, 7.61%; N, 6.61%; Found: C, 67.87%; H, 7.81%; N, 6.19%.

Example 11
1-(3-(Phenothiazin-10-yl)-1-propyl)-4-piperidinecarboxylic acid hydrochloride

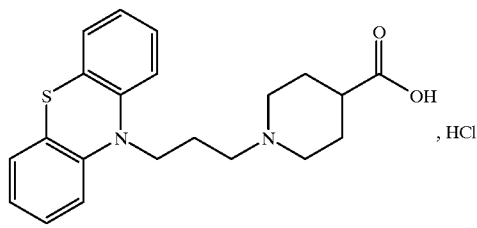

HPLC retention time=20.13 minutes (5 μm C18 4×250 mm column, eluting with a 20–80% gradient of 0.1% trifluoroacetic acid/acetonitrile and 0.1% trifluoroacetic acid/water over 30 minutes at 35° C.).

$^1$H NMR (400 MHz, DMSO-d$_6$): $\delta_H$ 3.94 (t, 2H); 7.00 (t, 2H); 7.08 (d, 2H); 7.20 (m, 4H).

Example 12
(R)-1-(2-(10,11-dihydro-5H-dibenzo[a,d]cyclohepten-5-ylidene)-1-ethyl)-2-piperidinecarboxylic acid hydrochloride

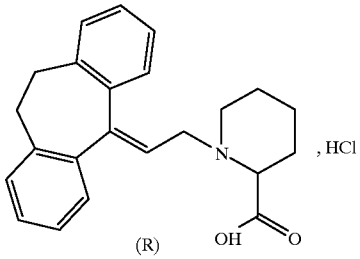

To a solution of 2-(10,11-dihydro-5H-dibenzo[a,d]cyclohepten-5-ylidene)ethyl bromide (2.36 g, 0.0079 mol) in dry N,N-dimethylformamide (11.8 ml) (R)-2-piperidinecarboxylic acid ethyl ester hydrochloride (2.30 g, 0.0119 mol) and potassium carbonate (3.28 g) were added. The reaction mixture was heated at 74–78° C. for 2.5 h. Water (40 ml) and benzene (40 ml) were added and after separation the organic phase was washed with water (2×40 ml), dried (MgSO$_4$) and the solvent was evaporated in vacuo. The residue was purified by column chromatography on silica gel (50 g) using chloroform as eluent. This afforded 3.11 g (R)- 1-(2-(10,11-dihydro-5H-dibenzo[a,d]cyclohepten-5-ylidene)-1-ethyl)-2-piperidinecarboxylic acid ethyl ester as an oil.

TLC: R$_f$: 0.5 (SiO$_2$: n-hexane/ethyl acetate=1:1).

The above ester was dissolved in ethanol (65 ml) and a solution of 4 N sodium hydroxide (8.8 ml) was added. The mixture was stirred at room temperature for six days. Concentrated hydrochloric acid (4.5 ml) was added followed by dichloromethane (445 ml). The phases were separated, the organic phase was dried (MgSO$_4$) and evaporated in vacuo. The residue (foam) was stirred overnight with diethyl ether (50 ml). This afforded, after drying, 2.2 g (73%) of the title compound as crystals.

M.p. 185–190° C.

Calculated for $C_{23}H_{25}$,NO, HCl: C, 71.95%; H, 6.83%; N, 3.65%; Found: C, 71.84%; H, 6.84%; N, 3.32%.

Example 13
1-(2-(10,11-Dihydro-5H-dibenzo[a,d]cyclohepten-5-ylidene)-1-ethyl)-4-piperidinecarboxylic acid hydrochloride

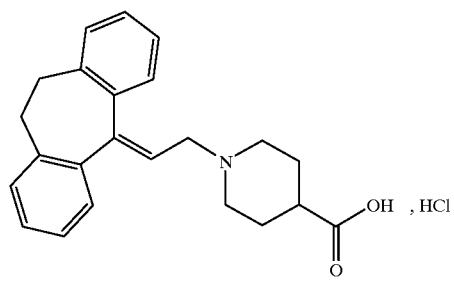

To a solution of 2-(10,11-dihydro-5H-dibenzo[a,d]cyclohepten-5-ylidene)ethylbromide (2.99 g, 0.01 mol) in dry N,N-dimethylformamide (15 ml), 4-piperidinecarboxylic acid ethyl ester (2.36 g, 0.015 mol)

and potassium carbonate (2.07 g, 0.0149 mol) were added. The reaction mixture was heated at 74–80° C. for 2.5 h. Water (50 ml) and benzene (50 ml) were added and after separation of the layers, the organic phase was washed with water (3×20 ml), dried (MgSO$_4$) and the solvent evaporated in vacuo. The residue was purified by column chromatography on silica gel (50 g) using chloroform as eluent. This afforded 2.17 g (58%) of 1-(2-(10,11-dihydro-5H-dibenzo [a,d]cyclohepten-5-ylidene)-1-ethyl)-4-piperidinecarboxylic acid ethyl ester as an oil.

The above ester (2.0 g, 0.0053 mol) was dissolved in ethanol (45 ml) and a solution of 4 N sodium hydroxide (6 ml) was added. The mixture was left at room temperature for 24 h. Concentrated hydrochloric acid (3.0 ml) was added followed by dichlormethane (300 ml). The phases were separated, the organic phase was dried (MgSO$_4$) and the solvent evaporated in vacuo. The oily residue was stripped with acetone (20 ml) and the solution left at room temperature for two days. The crystalline product was filtered and washed with acetone and n-hexane. After drying, this afforded, 1.18 g (58%) of the title compound.

M.p. 219–227 C.

Calculated for C$_{23}$H$_{25}$NO$_2$, HCl: C, 71.95%; H, 6.83%; Cl, 9.23%; N, 3.65%; Found: C, 71.54%; H, 6.87%; Cl, 8.94%; N, 3.80%.

Example 14

1-(2-(6,11-Dihydrodibenzo[b,e]oxepin-11-ylidene)-1-ethyl)-4-piperidinecarboxylic acid

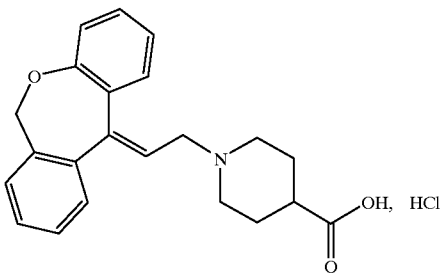

To a solution of 11-(2-bromoethylidene)-6,11-dihydrodibenzo[b,e]oxepine (4.55 g, 0.015 mol) in dimethylsulfoxide (90 ml), potassium carbonate (3.1 g, 0.0225 mol), 4-piperidinecarboxylic acid ethyl ester (2.36 g, 0.015 mol) and sodium iodide (50 mg) were added and the mixture was stirred at 70–80° C. for 5 h. The reaction mixture was diluted with benzene (250 ml), the solid was filtered off and the filtrate was washed with water (5×100 ml). The benzene solution was dried (MgSO$_4$) and the solvent removed in vacuo. The oily residue (4.94 g) was dissolved in acetone and treated with an ethanolic solution of oxalic acid. The precipitated crude hydrogen oxalate was filtered off and washed with hot acetone. Yield 4.15 g (59%) of 1-(2-(6,11-dihydrodibenzo[b,e]oxepin-11-ylidene)-1-ethyl)-4-piperidinecarboxylic acid ethyl ester hydrogen oxalate.

M.p. 209–213° C.

The above ester (3.32 g base liberated from the hydrogen oxalate, 0.0088 mol) was dissolved in ethanol (17 ml) and 4 N sodium hydroxide (5 ml) was added. The reaction mixture was stirred at room temperature for 18 h, then poured into dichloromethane (350 ml) and acidified with concentrated hydrochloric acid. The dichloromethane layer was separated, dried (MgSO$_4$) and evaporated in vacuo. The residue was stripped twice with acetone (15 ml) and dissolved in acetone (30 ml). The crystalline product was filtered off and washed with acetone. After drying, this afforded 1.85 g (55%) of the title compound as a crystalline product.

M.p. 210–218° C. (decomp.).

Calculated for C$_{22}$H$_{23}$NO$_3$, HCl C, 68.48%; H, 6.27%; Cl, 9.19%; N, 3.63%; Found: C, 65.14%; H, 6.24%; Cl, 8.93%; N, 3.57%.

We claim:

1. A compound selected from the group consisting of:
   1-(2-(6,11-dihydrodibenzo[b,e]thiepin-11-ylidene)-1-ethyl)-3-piperidinecarboxylic acid, or a pharmaceutically acceptable salt thereof;
   1-(2-(6,11-dihydrodibenzo[b,e]thiepin-11-ylidene)-1-ethyl)-4-piperidinecarboxylic acid, or a pharmaceutically acceptable salt thereof;
   1-(3-(2-bromo-10,11-dihydro-5H-dibenzo[a,d]cyclohepten-5-ylidene)-1-propyl)-3-pyrrolidineacetic acid, or a pharmaceutically acceptable salt thereof;
   1-(3-(3-methyl-10,11-dihydro-5H-dibenzo[a,d]cyclohepten-5-ylidene)-1-propyl)-3-pyrrolidineacetic acid, or a pharmaceutically acceptable salt thereof;
   1-(3-(2-fluoro-10,11-dihydro-5H-dibenzo[a,d]cyclohepten-5-ylidene)-1-propyl)-4-piperidinecarboxylic acid, or a pharmaceutically acceptable salt thereof;
   1-(3-(phenothiazin-10-yl)-1-propyl)-4-piperidinecarboxylic acid, or a pharmaceutically acceptable salt thereof;
   (R)-1-(2-(10,11-dihydro-5H-dibenzo[a,d]cyclohepten-5-ylidene)-1-ethyl)-2-piperidinecarboxylic acid, or a pharmaceutically acceptable salt thereof;
   1-(2-(10,11-dihydro-5H-dibenzo[a,d]cyclohepten-5-ylidene)-1-ethyl)-4-piperidinecarboxylic acid, or a pharmaceutically acceptable salt thereof; and
   1-(2-(6,11-dihydrodibenzo[b,e]oxepin-11-ylidene)-1-ethyl)-4-piperidinecarboxylic acid, or a pharmaceutically acceptable salt thereof.

2. A compound of claim 1 which is 1-(2-(6,11-dihydrodibenzo[b,e]thiepin-11-ylidene)-1-ethyl)-3-piperidinecarboxylic acid, or a pharmaceutically acceptable salt thereof.

3. A compound of claim 1 which is 1-(2-(6,11-dihydrodibenzo[b,e]thiepin-11-ylidene)-1-ethyl)-4-piperidinecarboxylic acid, or a pharmaceutically acceptable salt thereof.

4. A compound of claim 1 which is 1-(3-(2-bromo-10,11-dihydro-5H-dibenzo[a,d]cyclohepten-5-ylidene)-1-propyl)-3-pyrrolidineacetic acid, or a pharmaceutically acceptable salt thereof.

5. A compound of claim 1 which is 1-(3-(3-methyl-10,11-dihydro-5H-dibenzo[a,d]cyclohepten-5-ylidene)-1-propyl)-3-pyrrolidineacetic acid, or a pharmaceutically acceptable salt thereof.

6. A compound of claim 1 which is 1-(3-(2-fluoro-10,11-dihydro-5H-dibenzo[a,d]cyclohepten-5-ylidene)-1-propyl)-4-piperidinecarboxylic acid, or a pharmaceutically acceptable salt thereof.

7. A compound of claim 1 which is 1-(3-(phenothiazin-10-yl)-1-propyl)-4-piperidinecarboxylic acid, or a pharmaceutically acceptable salt thereof.

8. A compound of claim 1 which is (R)-1-(2-(10,11-dihydro-5H-dibenzo[a,d]cyclohepten-5-ylidene)-1-ethyl)-2-piperidinecarboxylic acid, or a pharmaceutically acceptable salt thereof.

9. A compound of claim 1 which is 1-(2-(10,11-dihydro-5H-dibenzo[a,d]cyclohepten- 5-ylidene)-1-ethyl)-4-piperidinecarboxylic acid, or a pharmaceutically acceptable salt thereof.

10. A compound of claim 1 which is 1-(2-(6,11-dihydrodibenzo[b,e]oxepin-11-ylidene)-1-ethyl)-4-piperidinecarboxylic acid, or a pharmaceutically acceptable salt thereof.

11. A pharmaceutical composition comprising as an active component an effective amount of a compound of claim 1 together with a pharmaceutically acceptable carrier or diluent.

12. The pharmaceutical composition according to claim 11 comprising between 0.5 mg and 1000 mg of the compound per unit dose.

13. A method of treating neurogenic pain or inflammation comprising administering to a subject in need thereof an effective amount of a compound of claim 1.

14. A method of treating neurogenic pain or inflammation associated with neuropathy, rheumatoid arthritis, migraine or itching, comprising administering to a subject in need thereof an effective amount of a compound of claim 1.

15. A method of treating neurogenic pain or inflammation comprising administering to a subject in need thereof a pharmaceutical composition of claim 12.

16. A method of treating neurogenic pain or inflammation associated with neuropathy, rheumatoid arthritis, migraine or itching, comprising administering to a subject in need thereof a pharmaceutical composition of claim 12.

17. A method of reducing blood glucose and/or inhibiting the activity of CGRP comprising administering to a subject in need thereof an effective amount of a compound of claim 1.

18. A method of reducing blood glucose and/or inhibiting the activity of CGRP comprising administering to a subject in need thereof a pharmaceutical composition of claim 12.

* * * * *